United States Patent [19]

Granger

[11] Patent Number: 5,116,358
[45] Date of Patent: May 26, 1992

[54] COMBINED SURGICAL NEEDLE-SUTURE DEVICE POSSESSING A CONTROLLED SUTURE SEPARATION FEATURE

[75] Inventor: Richard N. Granger, Huntington, Conn.

[73] Assignee: United States Surgical Corporation, Norwalk, Conn.

[21] Appl. No.: 556,737

[22] Filed: Jul. 23, 1990

[51] Int. Cl.$^5$ .............................................. A61B 17/00
[52] U.S. Cl. ...................................... 606/224; 606/226
[58] Field of Search ................................. 606/222-227

[56] References Cited

U.S. PATENT DOCUMENTS

| | | |
|---|---|---|
| 86,769 | 2/1869 | Marriott . |
| 295,612 | 3/1884 | Bailey . |
| 299,305 | 5/1884 | Weed . |
| 877,476 | 1/1808 | Bach . |
| 1,106,667 | 8/1914 | Minahan . |
| 1,250,114 | 12/1917 | Bigelow et al. . |
| 1,558,037 | 10/1925 | Morton ........................ 606/222 |
| 1,591,021 | 7/1926 | Davis ............................ 606/224 |
| 1,613,206 | 1/1927 | Souttar . |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. ................. 606/225 |
| 2,302,986 | 11/1942 | Vollrath . |
| 2,411,079 | 11/1946 | Baule . |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,704 | 7/1968 | Dery . |
| 3,416,534 | 12/1968 | Quinn . |
| 3,799,169 | 3/1974 | Beroff et al. . |
| 3,835,912 | 9/1974 | Kristensen et al. . |
| 3,875,946 | 4/1975 | Duncan ......................... 606/227 |
| 3,880,167 | 4/1975 | Hardwick ..................... 606/225 |
| 3,890,975 | 6/1975 | McGregor . |
| 3,910,282 | 10/1975 | Messer et al. . |
| 3,918,455 | 11/1975 | Coplan ......................... 606/224 |
| 3,924,630 | 12/1975 | Walldorg . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter . |
| 3,980,177 | 9/1976 | McGregor . |
| 3,981,307 | 9/1976 | Borysko ....................... 606/224 |
| 4,054,144 | 10/1977 | Hoffman et al. ............. 606/226 |
| 4,072,041 | 2/1978 | Hoffman et al. ............. 606/226 |
| 4,124,027 | 11/1978 | Boss ............................. 606/226 |
| 4,127,133 | 11/1978 | Martinez . |
| 4,169,477 | 10/1979 | Bokros . |
| 4,359,053 | 11/1982 | Benjamin ..................... 606/226 |
| 4,411,654 | 10/1983 | Boarini et al. ............... 428/36 |
| 4,596,728 | 6/1986 | Yang et al. ................... 428/36 |
| 4,624,879 | 11/1986 | Van Dijck et al. . |
| 4,672,734 | 6/1987 | Kawada et al. . |
| 4,792,336 | 12/1988 | Hlavaceh et al. . |
| 4,799,483 | 1/1989 | Kraff ............................ 606/223 |
| 4,805,292 | 2/1989 | Noguchi ...................... 606/224 |
| 4,932,963 | 6/1990 | Ritter et al. ................. 606/224 |

FOREIGN PATENT DOCUMENTS 0358451 3/1990 European Pat. Off. .
2432861 3/1980 France .

*Primary Examiner*—Max Hindenburg
*Assistant Examiner*—Gary Jackson
*Attorney, Agent, or Firm*—Thomas R. Bremer; Peter G. Dilworth; Rocco S. Barrese

[57] ABSTRACT

Attachment of a surgical needle to a suture to provide a combined surgical needle-suture device employs a shrinkable tubing possessing a controlled suture separation feature.

18 Claims, 4 Drawing Sheets

COMBINED SURGICAL NEEDLE-SUTURE DEVICE POSSESSING A CONTROLLED SUTURE SEPARATION FEATURE

CROSS REFERENCE TO RELATED APPLICATION

This application relates by subject matter to commonly assigned, copending U.S. patent application Ser. No. 413,240, filed Sep. 27, 1989.

BACKGROUND OF THE INVENTION

The present invention relates to a method for attaching a surgical needle to a suture to provide a combined surgical needle-suture device possessing controlled suture separation characteristics and, more particularly, to such a method in which a lanced shrinkable tubing is employed to secure the needle to the suture yet providing for controlled separation of the suture from its needle when desired, e.g., at the conclusion of the suturing procedure.

For many years, surgeons have employed needle-suture combinations in which a suture or ligature is attached to the shank end of a needle. Such needle-suture combinations are provided for a wide variety of monofilament and braided suture materials, both absorbable and non-absorbable, e.g., catgut, silk, nylon, polyester, polypropylene, linen, cotton, and absorbable synthetic materials such as polymers and copolymers of glycolic and lactic acids.

Needle-suture combinations fall into two general classes: standard, or non-detachable, needle attachment and removable, or detachable, needle attachment. In the case of standard needle attachment, the suture is securely attached to the needle and is not intended to be separable therefrom, except by cutting or severing the suture. Removable needle attachment, by contrast, is such that the needle is separable from the suture in response to a force exerted by the surgeon. Minimum acceptable forces required to separate a needle from a suture (for various suture sizes) are set forth in the *United States Pharmacopoeia* (USP). The *United States Pharmacopoeia* prescribes minimum individual pull-out forces and minimum average pull-out forces as measured for five needle-suture combinations. The minimum pull-out forces for both standard and removable needle-suture attachment set forth in the *United States Pharmacopoeia* are hereby incorporated by reference.

One typical method for securing a suture to a needle involves providing a cylindrical recess in the shank end of a needle and securing a suture therein. For example, U.S. Pat. No. 1,558,037 teaches the addition of a cement material to such a substantially cylindrical recess to secure the suture therein. Additional methods for bonding a suture within a needle bore are described in U.S. Pat. Nos. 2,928,395 (adhesives) and 3,394,704 (bonding agents). Alternatively, a suture may be secured within an axial bore in a needle by swaging the needle in the region of the recess. See, e.g., U.S. Pat. No. 1,250,114. Additional prior art methods for securing a suture within a needle bore include expansion of a catgut suture through the application of heat (U.S. Pat. No. 1,665,216), inclusion of protruding teeth within the axial bore to grasp an inserted suture (U.S. Pat. No. 1,678,361) and knotting the end of the suture to be inserted within the bore to secure the suture therein (U.S. Pat. No. 1,757,129).

Methods for detachably securing a suture to a needle are also well known. For example, U.S. Pat. Nos. 3,890,975 and 3,980,177 teach swaging a suture within a needle bore such that the suture has a pull-out valve of 3 to 26 ounces. Alternative detachable attachment methods include providing a weakened suture segment (U.S. Pat. No. 3,949,756), lubricant tipping the end of a suture to be inserted in the axial bore of a needle (U.S. Pat. No. 3,963,031) and pre-tensioning a suture that is swaged within an axial needle bore (U.S. Pat. No. 3,875,946). See also, U.S. Pat. Nos. 3,799,169; 3,880,167; 3,924,630; 3,926,194; 3,943,933; 3,981,307; 4,124,027; and, 4,127,133.

Another method for attaching a suture to a needle involves the use of tubing which is secured to the shank end of the needle and to the suture. For example, U.S. Pat. No. 1,613,206 describes the use of a tubing (preferably silver) which is secured to the shank end of a needle and to a ligature. It is suggested that the tube may be attached to the needle by pressure or soldering and to the ligature by pressure or cementing. It is also suggested that the shank of the needle be of reduced cross section and that the furthest extremity of the reduced diameter shank section be provided with a spike or point upon which the suture may be secured prior to tube application.

U.S. Pat. No. 2,240,330 describes a tubing attachment method whereby the tubing and suture are releasably secured to the needle. In particular, the needle and tubing are provided with cooperating catch and abutment means which are released one from the other by rotating the needle 90° relative to the tubing (or vice versa). The tubing is manufactured from spring-tempered carbon steel or chrome nickel steel and is secured to the suture by heating the tubing and then swaging to the suture.

U.S. Pat. No. 3,311,100 relates to a flexible composite suture having a tandem linkage The needle is secured to a flexible suture leader manufactured from a readily sterilizable plastic such as nylon, linear polyethylene, isotactic polypropylene, polyester, silk or other proteinaceous material, e.g., by inserting and crimping the leader within an axial bore in the needle shank. The opposite end of the suture leader is crimped within a connector sleeve of a thin walled metal tubing, e.g., stainless steel. The opposite end of the tubing is crimped around a stiff suture, e.g., monofilament stainless steel.

U.S. Pat. No. 3,918,455 describes a needle-suture attachment wherein a hollow suture portion is secured to the shank end of a needle which is of reduced cross-section as compared to the remainder of the needle.

Additional patents which describe the use of tubing to effect suture-needle attachment include U.S. Pat. Nos. 4,672,734 (forming needle from U-shaped metal plate around suture), 4,359,053 (silicone tubing), 3,835,912 (laser welding of metal tube to needle), 2,814,296, 2,802,468 (chamfered tubing ends), 2,302,986, 2,240,330, 1,981,651 (needle and tubing screw threaded), 1,960,117, and 1,591,021.

Numerous disadvantages exist with methods used heretofore to effect needle-suture attachment. For example, those methods which involve the formation and use of an axial bore in the shank end of the needle require the use of expensive hole forming equipment. Moreover, it is difficult to maintain the bore concentric with the center-line of the needle and to control the depth (and diameter) of the bore when drilling the needle shank, whether using conventional drilling equipment or laser drilling. Another disadvantage is the possibility that foreign substances may inadvertently or uncontrollably be introduced into the needle bore, e.g., oil used during drilling or silicone from the needle silconization process. Safeguards employed in an attempt to prevent the introduction of such foreign materials, e.g., water blocking during needle silconization, are inconvenient adding time, effort and cost to the needle production process.

Attachment processes which employ bored needle shanks also limit the range of materials from which needles may be fabricated in a cost effective fashion. For example, it is exceedingly difficult to drill Series 300 stainless steel (laser drilling is required) and, once drilled, it is difficult to swage Series 300 stainless steel in a consistent and reliable manner. For this reason, Series 300 stainless steel is not employed for the vast majority of needled suture products despite its advantageous combination of strength and ductility characteristics as compared to conventionally employed Series 400 stainless steel.

Additional disadvantages associated with needle-suture attachment methods which employ bored needle shanks include the weakness imparted to the bored section of the needle, particularly after swaging, and the attendant increased possibility that the needle will fracture in this region. It is also difficult to provide a specialized surface finish to the needle shank to assist in needle attachment, e.g., a texturized surface and/or a tapered bore. Swaging equipment used in such needle-suture attachment methods is also maintenance intensive.

Needle-suture attachment methods which have employed tubings heretofore also exhibit numerous disadvantages. Methods which employ metal tubings greatly diminish the flexibility of the needle-suture combination in the attachment region Such diminished flexibility has a deleterious effect in many surgical procedures. Swaging of the tubing to the needle and the suture is also undesirable in that swaging is time-consuming, maintenance intensive, and subject to variability in attachment force.

Moreover, needle-suture attachment methods which have employed tubings heretofore have necessarily required the use of tubing having an inner diameter essentially equal to the outer diameters of the needle shank and suture tip to be attached. Too large a difference between the aforesaid inner and outer diameters inhibits the attachment process, and prevents a tight, secure interface between needle (and/or suture) and tubing. The limited tolerance between the tubing inner diameter and the needle shank/suture outer diameters in such methods make these dimensions critical, thereby making the attachment process more difficult and time-consuming, and increasing the likelihood of attachment failure and/or rejected materials.

In addition to the needle-suture constructions of the aforedescribed pull-out variety, it is known from U.S. Pat. No. 4,805,292 to provide a needle-suture combination in which a suture cutting edge is formed at the shank end of the needle. However, the combined needle-suture device of U.S. Pat. No. 4,805,292, like others described above, possesses a suture tip-receiving axial bore, or recess, formed in the butt end of the needle and as such is subject to the disadvantages recounted above which are associated with a needle possessing an axial bore.

SUMMARY OF THE INVENTION

In accordance with the present invention, there is provided a method for attaching a surgical needle to a suture to provide a combined surgical needle-suture device possessing a controlled suture separation feature which comprises:

a) providing a needle possessing a shank end of reduced diameter;

b) providing a suture, one tip region of which is to be attached the shank end of the needle;

c) placing a shrinkable tubing, one section of which possesses a lance-forming region, around the reduced diameter shank end of the needle and around the tip region of the suture such that the lance-forming region of the tubing is adjacent to the tip region of the suture;

d) applying energy to the shrinkable tubing to bring the tubing into engagement with at least the shank end of the needle; and, e) depressing the lance-forming region of the tubing to form a lance in engaging, but controllably separable, contact with the tip region of the suture thereby providing the combined surgical needle-suture device with its controlled separation feature.

In addition to the foregoing surgical needle-suture attachment method, the present invention includes the resulting combined surgical needle-suture device.

BRIEF DESCRIPTION OF THE DRAWINGS

The present invention will become more apparent from the following detailed description taken in conjunction with the accompanying drawings in which.

DETAILED DESCRIPTION OF THE INVENTION

The present invention relates to a method for securing a surgical needle to a suture to provide a combined surgical needle-suture device possessing a controlled suture separation feature. The invention has application to any suture material whether absorbable or non-absorbable, natural or synthetic, braided or monofilament, and to any needle material and configuration whether straight or curved.

Figure 1:
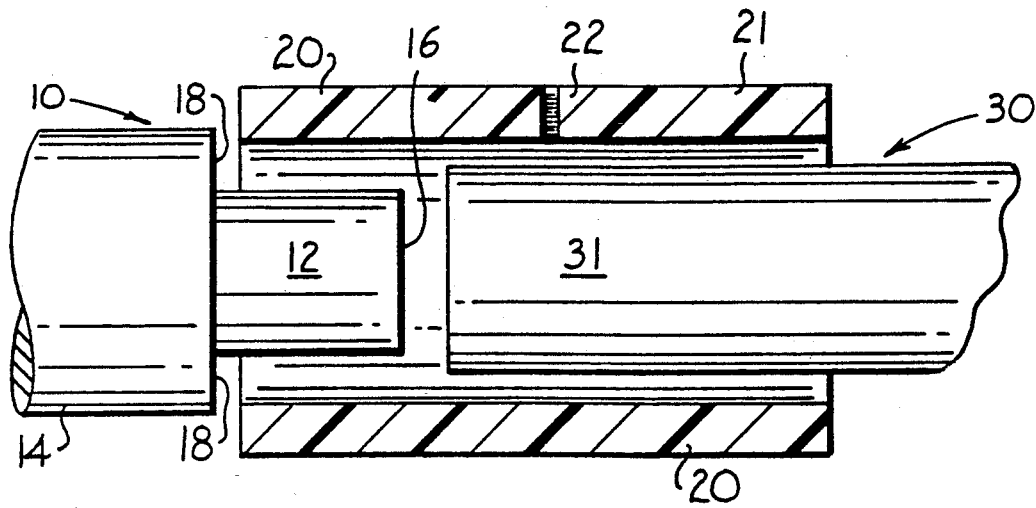
FIG. 1 is a side cross-sectional view of a portion of a surgical needle and a portion of a suture which is to be attached to the needle, the needle and suture portions being shown loosely inserted into the opposite ends of a shrinkable tubing possessing a lance forming region.
Figure 2:
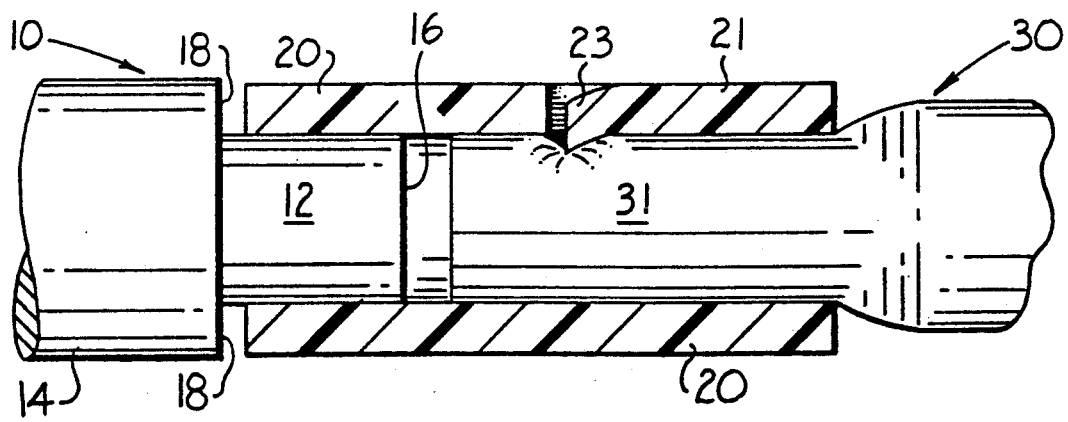
FIG. 2 is a side cross-sectional view of the needle and suture of FIG. 1 following contraction of the tubing around both the shank end of the needle and the tip region of the suture and following depression of the lance-forming region to provide a lance in engaging, but controllably separable, contact with the tip region of the suture.
Figure 3:
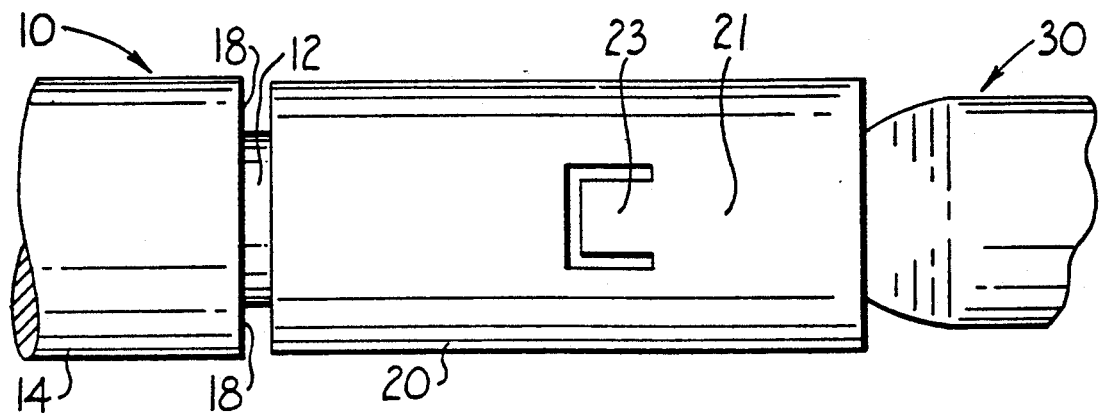
FIG. 3 is a top exterior view of the combined surgical needle-suture device of FIG. 2.
Figure 5:
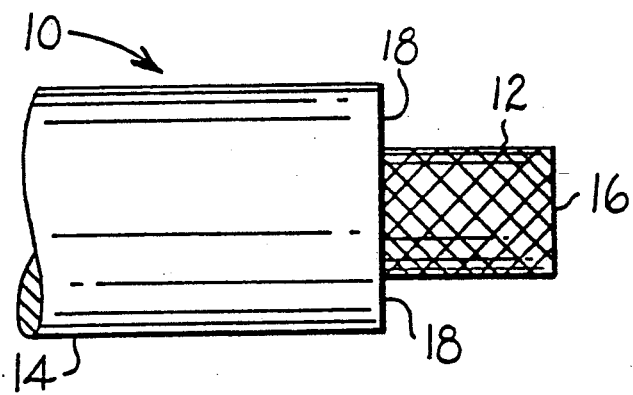
FIG. 5 is a side view of an alternative embodiment of the present invention in which the shank end of the needle is scored.
Figure 6:
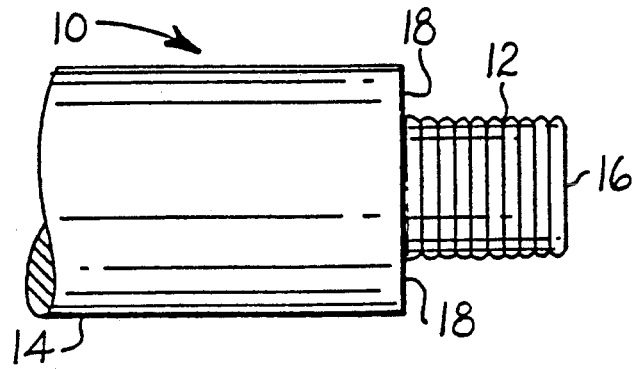
FIG. 6 is a side view of an alternative embodiment of the present invention in which the needle shank end is ribbed.
Figure 7:
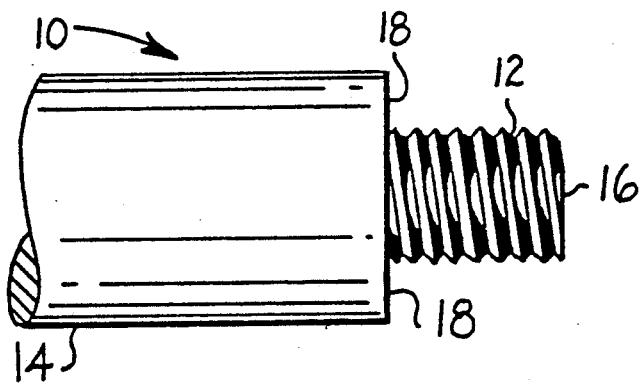
FIG. 7 is a side view of an alternative embodiment of the present invention in which the needle shank end is threaded.
Figure 8:
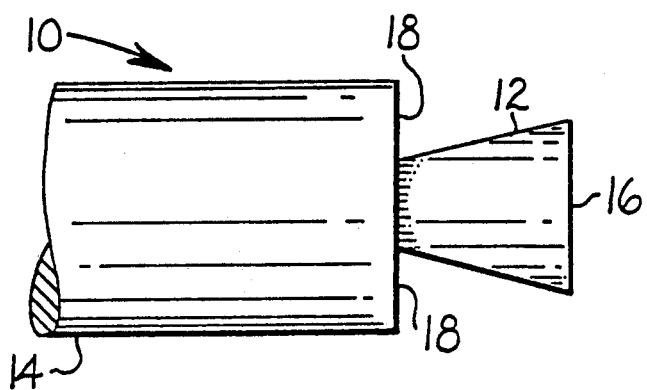
FIG. 8 is a side view of an alternative embodiment of the present invention in which the needle shank end is tapered to expand in a directional way from a remainder of the needle.
Figure 9:
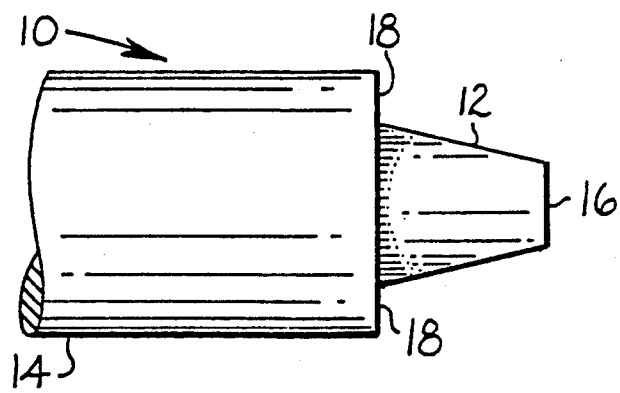
FIG. 9 is a side view of an alternative embodiment of the present invention in which the needle shank end is tapered to expand in a direction toward the remainder of the needle.

Referring to FIGS. 1-3, needle 10 has a reduced cross-sectional diameter at its shank end 12 relative to the remaining portion 14 of the needle. The diameter of shank end 12 can be reduced by any conventional means, e.g., by machining on a lathe. Typically, shank end 12 has a diameter from 10 to 65% smaller than the remaining portion 14 of the needle, and preferably from 25 to 50% smaller. It is also possible to provide shank end 12 with a texturized surface to facilitate gripping by shrinkable tubing 20. For example, shank end 12 may be scored, ribbed or threaded, in whole or in part (FIGS. 5-7 respectively). It may also be desirable to taper shank end 12 such that its distal end 16 is of greater cross-sectional diameter than the cross-sectional diameter of shank end 12 in the region of shoulder 18, or vice versa (FIGS. 8 and 9 respectively). Region 21 of shrinkable tubing 20 which is adjacent tip region 31 of suture 30 possesses a depressible lance-forming region 22 which, when depressed as shown in FIG. 2, provides a lance 23 of which more will be described below. Shank end 12 of needle 10 is placed within one end of shrinkable tubing 20 and tip region 31 of suture 30 is placed within the other end of shrinkable tubing 20. Distal end 16 of shank end 12 may abut the end of suture 30 or be separated a short distance therefrom as shown in FIGS. 1 and 2.

As shown in FIG. 1, suture 30 may initially be of uniform cross-section throughout its length. Alternatively, tip region 31 of the suture, i.e., the region of the suture inserted into one end of shrinkable tubing 20, may be of reduced cross-section relative to the remainder of the suture. This can be achieved by tipping suture tip region 31 with an adhesive or resinous tipping agent while suture 30 is under tension. (See, e.g., Canadian Patent No. 1,009,532.) Resin tipping may be desirable to prevent brooming of the suture, particularly for multifilament braided sutures, by rigidifying the tip region of the suture thus facilitating its handling during the attachment process. Reducing the diameter of the suture tip, as by tipping under tension, may be desirable to allow a suture of larger diameter, e.g., a suture diameter equal to the diameter of the needle to which it is to be attached, to be more readily attached to the needle. It is not necessary, however, to reduce the diameter of suture tip region 31 to effectively attach needle 10 to suture 30. Indeed, it may be possible or desirable to apply a tipping agent to prevent brooming without reducing suture diameter. As shown in FIG. 1, shrinkable tubing 20 initially has an inner diameter which is larger than the outer diameter of the tip region of suture 30, thereby minimizing any advantage to suture tipping.

The expression "shrinkable tubing" is intended to include a tubing which may be shrinkable for its entire length, e.g., as shown in FIGS. 1-3, but is at least shrinkable for that region which is to engage shank end 12 of needle 10. Thus, tubing 20 can be fabricated entirely from a shrinkable material or it can be a bicomponent device as shown in FIG. 4, one component of which is shrinkable and is intended to engage needle shank end 12 and the other component of which is shrinkable or non-shrinkable and achieves attachment to the suture at least in part by means of a lance formed thereon.

Figure 4:
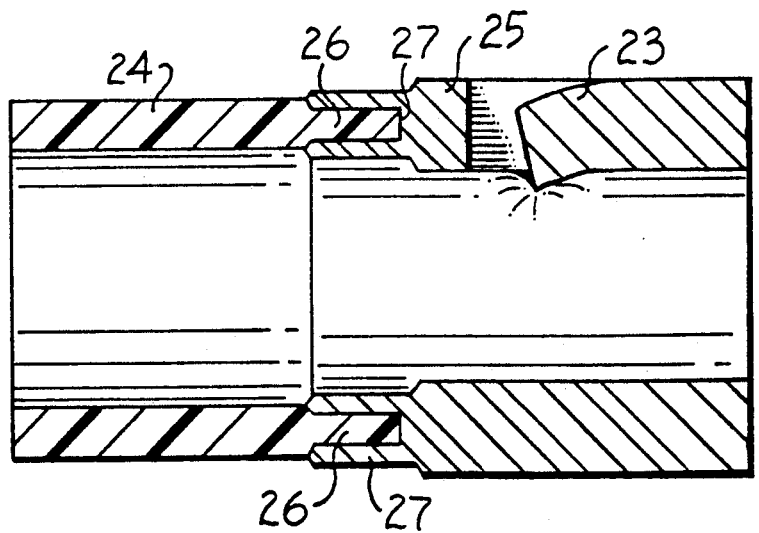
FIG. 4 is another type of tubing which can be used to achieve attachment of the suture to the needle and features a shrinkable component and a lanced non-shrinkable component.

Where, as in the embodiment of FIGS. 1-3, tubing 20 is shrinkable for its entire length, it must possess a sufficient stiffness to provide an effective lance member 23, i.e., once formed, the lance will tend to remain in the position shown in FIG. 2, compressing suture 30 against the interior wall of the tubing and thereby effecting attachment of the suture to the needle. Suitable materials for the construction of an entirely shrinkable tubing include "memory metals" e.g., nickel-titanium mixtures, or copper based materials, as are well known in the art (see, e.g., U.S. Pat. Nos. 3,759,552, 3,801,954, 4,198,081 and 4,733,680) available from Raychem Corporation, Menlo Park, Calif.

Where tubing 20 is a bicomponent device as shown in FIG. 4, shrinkable component 24 can be a "memory metal" as just recited or it can be fabricated from a "memory plastic", e.g., a polyvinylidene fluoride material available from Raychem Corporation (RT-850) which shrinks at temperatures of greater than 175° C. and can recover to within about 50% of its radially expanded inner diameter. Component 25 of bicomponent tubing 20 must, of course, be of sufficient stiffness to provide lance element 23, a condition generally satisfied by most metals including the shrinkable metals mentioned above. Attachment of both components of the tubing can be achieved in any known or conventional manner, e.g, by inserting edge 26 of shrinkable component 24 into annular groove 27 formed in the facing edge of component 25 followed by crimping the walls of the groove to firmly secure the edge of the shrinkable component therein.

Returning to the embodiment of FIGS. 1-3, after shrinkable tubing 20 has been placed around shank end 12 of needle 10 and suture tip region 31, energy is applied to the tubing. In response to this energy, tubing 20 shrinks or contracts thereby engaging shank end 12 of the needle and the suture tip region 31. The overall length of tubing 20 may also be affected by the application of energy, e.g., the length of tubing 20 may undergo reduction to some extent. Suitable energy sources for shrinking tubing 20 include heat (convective or conductive), radiation, microwave energy, etc.

As shown in FIGS. 1-2, shrinkable tubing 20 is simultaneously placed around both suture tip region 31 and shank end 12 of needle 10 in one embodiment of the present invention It is preferable, however, to sequentially secure tubing 20 to needle 10 and suture tip region 31. Thus, in a preferred embodiment of the present invention, shrinkable tubing 20 is initially secured to shank end 12 through the localized application of energy to tubing 20 in the region surrounding shank end 12. After tubing 20 has been brought into engagement with shank end 12, tip region 31 of suture 30 is inserted into tubing 20 and additional energy is applied thereto. Sequential shrinkage of tubing 20 makes it possible to vary the amount of energy used in securing tubing 20 to shank end 12 and suture tip region 31, respectively, and to limit the exposure of suture 30 to energy during the attachment process. It may also be desirable to cool suture 30 in the region outside tubing 20 to prevent any undesirable degradation thereof, e.g., employing a curtain of cool air.

As shown in FIGS. 2-4, the shrinkage of tubing 20 typically compresses tip region 31 of suture 30 to some extent. This is particularly true where the suture is a braided, multi-filament material having void spaces in its structure. For example, tubing 20 may compress the tip region 31 by as much as 30 to 35% for a braided, synthetic absorbable suture and by a minimal amount for a relatively stiff material such as a monofilament surgical gut.

The amount of energy applied to the tubing to effect the desired attachment, i.e., diameter reduction, depends upon the characteristics of the tubing material, the relative dimensions of the tubing, the shank end of the needle and the suture and the desired pull-out force for the needle-suture combination. Tubing 20 can be heated through contact with a hot gas stream or with heated dies or by other suitable heating means. Typically, the outer diameters of shank end 12 and suture tip region 31 are greater than the fully recovered diameter of tubing 20 such that tubing 20 engages shank end 12 and the suture tip region 31 It is preferred that the attachment conditions be controlled such that the tubing remains secured to the needle once the suture is detached.

Following attachment of the tubing to the needle and suture, lance-forming region 22 is depressed, e.g., employing a punch or similar means, to form lance 23 which compresses suture tip region 31 against the interior wall of tubing 20. The amount of compressive force exerted by lance element 23 against suture tip region 31 can be readily varied to provide a suture separation, or pull-out, force within a predetermined range, e.g., that set forth in the *United States Pharmacopoeia*.

In the case of the alternative tubing embodiment of FIG. 4, once shrinkable component 24 of the tubing has been constricted around needle shank end 12, the lance forming element present on non-shrinkable component 25 (equivalent to section 22 of tubing 20 of FIG. 1) is depressed thereby compressing the suture to complete the needle-suture attachment sequence.

The foregoing surgical needle-suture attachment procedure has many advantages over previous attachment methods. Machining of the needle to provide a reduced diameter needle shank is much easier and more controllable than drilling processes, and permits the use of needle alloys which have previously been impractical, e.g., Series 300 stainless steel and MP35N (available from SPS Technologies) These heretofore impractical alloys have advantageous strength and ductility characteristics as compared to conventionally used Series 400 stainless steels. Moreover, an unreliable, expensive and maintenance intensive swaging process is replaced by a sterile, controllable and relatively inexpensive energy supply.

The attachment method is also much more efficient from a processing and inventory control standpoint. For example, the tubing may be removed from a needle and the needle attached to a fresh suture, e.g., in instances where the suture and/or attachment properties of the initial suture-needle combination are outside specifications. In many instances, the suture may also be recovered and reused, thereby greatly reducing processing waste. The range of acceptable suture diameters is greatly expanded due to the 0 ability of the tubing to recover or shrink to varying degrees, thereby minimizing the likelihood that suture production will be rejected for inability to attach several needle sizes because the shrinkable tubing is capable of recovering or shrinking to varying degrees. This greatly simplifies inventory considerations. Moreover, the needle-suture combinations are atraumatic and advantageously exhibit flexibility in the attachment region.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto

What is claimed is:

1. A method for attaching a surgical needle to a suture to provide a combined surgical needle-suture device possessing a controlled suture separation feature which comprises:
    a) providing a needle possessing a shank end of reduced diameter;
    b) providing a suture, one tip region of which is to be attached the shank end of the needle;
    c) placing a shrinkable tubing, one section of which possesses a lance-forming region, around the reduced diameter shank end of the needle and around the tip region of the suture such that the lance-forming region of the tubing is adjacent to the tip region of the suture;
    d) applying energy to the shrinkable tubing to bring the tubing into engagement with at least the shank end of the needle; and,
    e) depressing the lance-forming region of the tubing to form a lance in engaging, but controllably separable, contact with the tip region of the suture thereby providing the combined surgical needle-suture device with its controlled separation feature.

2. The method of claim 1, wherein the shrinkable tubing couples the needle and suture without swaging or crimping.

3. A method for attaching a surgical needle to a suture to provide a combined surgical needle-suture device possessing a controlled suture separation feature which comprises:
    a) providing a needle possessing a shank end of reduced diameter;
    b) providing a suture, one tip region of which is to be attached to the shank end of the needle;
    c) placing a shrinkable tubing, one section of which possesses a lance-forming region around the reduced diameter shank end of the needle and around the tip region of the suture such that the lance-forming region of the tubing is adjacent to the tip region of the suture;
    d) applying energy to the shrinkable tubing to bring the tubing into engagement with at least the shank end of the needle; and,
    e) depressing the lance-forming region of the tubing to form a lance in engaging, but controllably separable contact with the tip region of the suture thereby providing the combined surgical needle-suture device with its controlled separation feature, wherein the tubing is fabricated from a memory metal or from a plastic.

4. The method of claim 2, wherein said metal or plastic is heat shrinkable.

5. A method for attaching a surgical needle to a suture to provide a combined surgical needle-suture device possessing a controlled suture separation feature which comprises:

a) providing a needle possessing a shank end of reduced diameter;
b) providing a suture, one tip region of which is to be attached to the shank end of the needle;
c) placing a shrinkable tubing, one section of which possesses a lance-forming region, around the reduced diameter shank end of the needle and around the tip region of the suture such that the lance-forming region of the tubing is adjacent to the tip region of the suture;
d) applying energy to the shrinkable tubing to bring the tubing into engagement with at least the shank end of the needle; and,
e) depressing the lance-forming region of the tubing to form a lance in engaging, but controllably separable, contact with the tip region of the suture thereby providing the combined surgical needle-suture device with its controlled separation feature.

wherein the tubing comprises a shrinkable component for engaging the shank end of the needle and a shrinkable or non-shrinkable component possessing the lance-forming region.

6. The method of claim 5 wherein the shrinkable component is fabricated from a memory metal or a memory plastic and the non-shrinkable component is fabricated from a metal.

7. A combined surgical needle-suture device possessing a controlled suture separation feature which comprises:
a) a needle possessing a shank end of reduced diameter;
b) a suture possessing a tip region abutting or proximate to, the shank end of the needle; and,
c) a tubing fabricated at least in part from a shrinkable material in engagement with the shank end of the needle and possessing a lance in engagement with the suture, wherein the tubing is fabricated from a memory metal or from a plastic.

8. The combined surgical needle-suture device of claim 7, wherein said metal or plastic is heat shrinkable.

9. A combined surgical needle-suture device possessing a controlled suture separation feature which comprises:
a) a needle possessing a shank end of reduced diameter;
b) a suture possessing a tip region abutting or proximate to, the shank end of the needle; and
c) a tubing fabricated at least in part from a shrinkable material in engagement with the shank end of the needle and possessing a lance in engagement with the suture, wherein the tubing comprises a shrinkable component engaging the shank end of the needle and a shrinkable or non-shrinkable component possessing the lance.

10. The combined surgical needle-suture device of claim 9 wherein the shrinkable component is fabricated from a memory metal or a memory plastic and the non-shrinkable component is fabricated from a metal.

11. The combined surgical needle-suture device of claim 9 wherein the memory plastic is a polyvinylidene fluoride.

12. A combined surgical needle-suture device possessing a controlled suture separation feature which comprises:
a) a needle possessing a shank end of reduced diameter;
b) a suture possessing a tip region abutting or proximate to, the shank end of the needle; and,
c) a tubing fabricated at least in part from a shrinkable material in engagement with the shank end of the needle and possessing a lance in engagement with the suture.

13. The combined surgical needle-suture device of claim 12, wherein the shank end is provided with a texturized surface to facilitate gripping by said shrinkable tubing.

14. The combined surgical needle-suture device of claim 13, wherein the shank end is scored, ribbed or threaded in whole or in part.

15. The combined surgical needle-suture device of claim 12, wherein the shank end of reduced cross-section forms a shoulder with a remainder of the needle.

16. The combined surgical needle-suture device of claim 15, wherein said shank end is tapered in a direction toward said shoulder, such that a distal end of said shank end is of greater cross-sectional diameter than cross-sectional diameter of said shank end in a region of said shoulder.

17. The combined surgical needle-suture device of claim 15, wherein said shank end is tapered in a direction away from said shoulder, such that a distal end of said shank end is of smaller cross-sectional diameter than cross-sectional diameter of said shank end in a region of said shoulder.

18. The combined surgical needle-suture device of claim 12, wherein said tubing couples said needle and suture without swaging or crimping.

* * * * *